US00PP08049P

United States Patent [19]

Swillen

[11] Patent Number: Plant 8,049

[45] Date of Patent: Dec. 1, 1992

[54] APPLE VARIETY JONAGOLD DE COSTER

[75] Inventor: Georges M. Swillen, Wersbeek, Belgium

[73] Assignee: The De Coster Group, Molenbeek-Wersbeek, Belgium

[21] Appl. No.: 619,447

[22] Filed: Nov. 29, 1990

[51] Int. Cl.[5] ..... A01H 5/00

[52] U.S. Cl. ..... Plt./34.1

[58] Field of Search ..... Plt. 34

[56] References Cited

U.S. PATENT DOCUMENTS

P.P. 5,937 4/1987 Monen-De Costes ..... Plt. 34
P.P. 6,148 4/1988 Ligonniere ..... Plt. 34
P.P. 7,146 2/1990 Schneider ..... Plt. 34
P.P. 7,590 7/1991 Lichtenauer ..... Plt. 34

OTHER PUBLICATIONS

Goddrie, P. D., et al., *Jonagold Color Varieties*, Proefstation Voor de Fruittelt, Wilhelmindorp, Belgium, Nov. 1990, 24 pages.

*Primary Examiner*—James R. Feyrer
*Attorney, Agent, or Firm*—Eugene D. Farley

[57] ABSTRACT

The Jonagold De Coster strain of Jonagold apple tree characterized particularly by the bright red color of its fruit, the high color percentage of its fruit, and by its freedom from virus infection.

4 Drawing Sheets

This invention relates to a new and distinct variety of apple tree named Jonagold De Coster, sometimes denominated "Decosta".

The new apple variety was discovered in a cultivated orchard located in MOLENBEEK-WERSBEEK, Hageland, Belgium as a spontaneous whole tree mutation of Jonagold (Unpatented). Neither this tree nor its parent had been treated in any manner designed to induce sports.

The new apple tree cultivar was one of the block of apple trees propagated on M9 rootstock with Jonagold budwood. Its most unique characteristic is its desirable fruit color.

With respect to fruit color, Jonagold De Coster exhibits a higher degree of color development than standard Jonagold. Although as the percentage of red color on the fruit increases with the season, the shade of red color remains throughout the season the bright wind red color that standard Jonagold is known for. Its color characteristics may best be summarized in the following Table.

| | Jonagold De Coster | Jonagored | Jonagold |
|---|---|---|---|
| Early color development of fruit | Similar to Standard Jonagold with some pink to red additional color visible from July through early September | Brownish brown-red color throughout the growing season, darkening and redening in early September | Light green to dark green |
| Fruit finish color - shade | Very bright wine red tone similar to standard Jonagold with no brown tones. Finish tone is between 818 Jasper red and 818 Orient red, RHCCL | Dark red to brown red; 821 Currant red to 822 Cardinal red, RHCCL | Bright, wine red with white to yellow background |
| Fruit finish color - % | Many fruits with 85%-95% red color, some light stripes | Many fruits with 85-95% red color, some apples blush finish, | Many fruits with 20-30% red |

-continued

| | | others bold stripes | color stripes over a white to yellow background |
|---|---|---|---|
| | Rubinstar | Daliguy | Jonica |
| Early color development of fruit | Starts very early- at the end August in a brownish way | Light green dark green | Light green |
| Fruit finish color - shade | Transforms from brown into dark red | Bright wine-red with white to yellow background | Brown to pink-red |
| Fruit finish color - % | Many fruits with 90-100% red color | Many fruits with 30-40% red color stripes over a white to yellow background with more intensity than standard | Many fruit colors with 70% in a pink-red. Others stay brownish pink red |

RHCCL — Royal Horticultural Colour Chart of London

With respect to virus, both the budwood and rootstock of the original mutation were controlled by the N.A.K.B. of Holland and labeled as virus free. The current scion wood in the U.S.A. also is virus free, as certified by the Washington State Department of Agriculture.

The new apple tree variety has been asexually propagated through three generations and its new characteristics shown to be stable and reproducible.

The three generations have been asexually propagated through T-budding and benchgrafting onto certified virus-free rootstocks. The trees of the first, second and third generation and 10,000 control trees in their second leaf in an orchard at Dronten, Holland have been controlled individually by the staff of the Belgian National Research Station, the Dutch Fruit Advisory Team, and the staff of the Dutch Government Research Bureau.

More than 150,000 trees produced apples in 1991 in orchards planted in Belgium, The Netherlands, France, and North, South and Eastern Germany. All the apples so produced were checked and found to be of uniform and stable color.

Also, the trees have been planted and observed in all of the research stations supervising apple variety trials in Europe. These stations are located in Velm, Belgium; Wilhelminadorp, Zeewolde, Numansdorp, Horst, Geldermalsen, The Netherlands; York, Ahrweiler, and Bavendorf, Germany; Haidegg, Austria; Laimburg, Italy; Angers, Marsillarges, France, and elsewhere in the world. In all of these stations Jonagold De Coster has been named among the best mutations of Jonagold.

IN THE DRAWINGS

Figure 1:
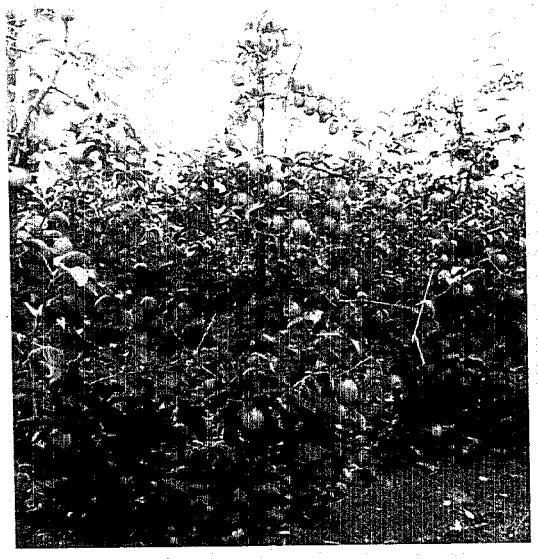
FIG. 1 is a view of the Jonagold De Coster apple tree variety of my discovery shown as it was discovered between a pair of standard Jonagold apple trees of the same stock, growing in the same block of trees.
Figure 2:
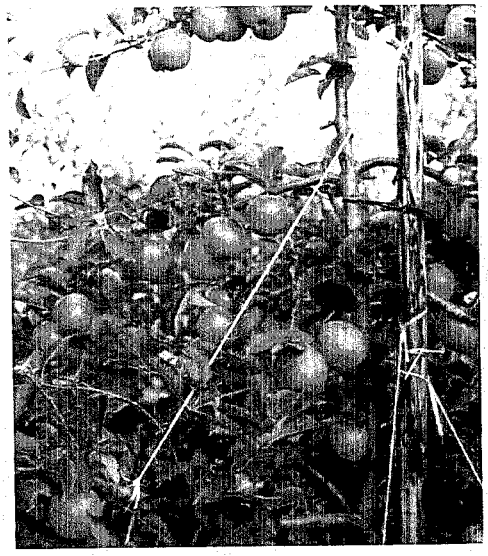
FIG. 2 is an enlarged view of the new variety, illustrating the manner in which it was grown in Belgium, slender spindle fashion, with wide branch angles.
Figure 3:
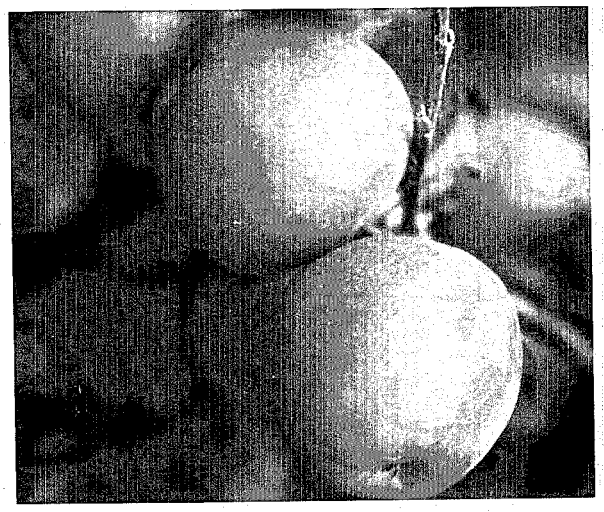
FIG. 3 is an enlarged view illustrating the appearance and color of the mature fruits of the new apple tree variety.
Figure 4:
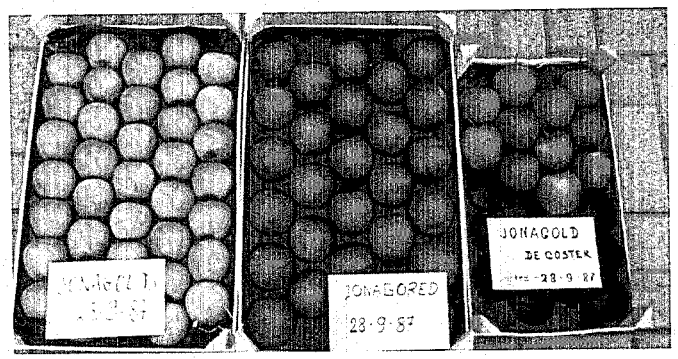
FIG. 4 is a comparative display of the fruits of the new apple variety in a mature state comparing them, with particular reference to color, with the standard Jonagold apple variety and the Jonagored apple variety in the same mature state.
Figure 5:
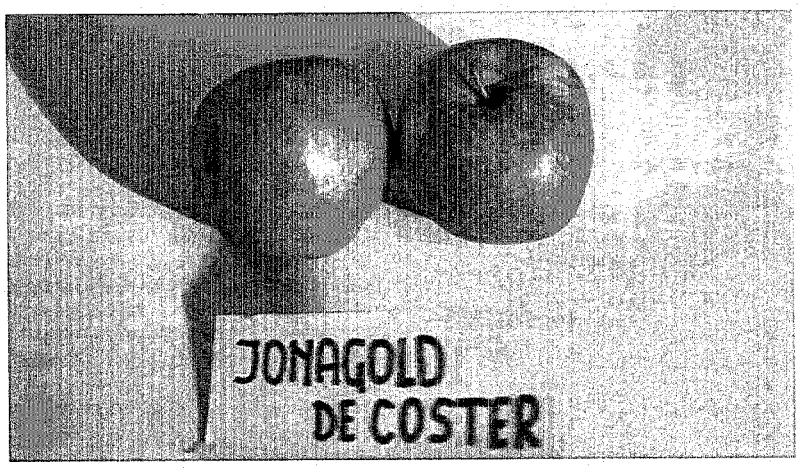
FIGS. 5 and 6 are elevational and sectional views, respectively of the new variety.
Figure 6:
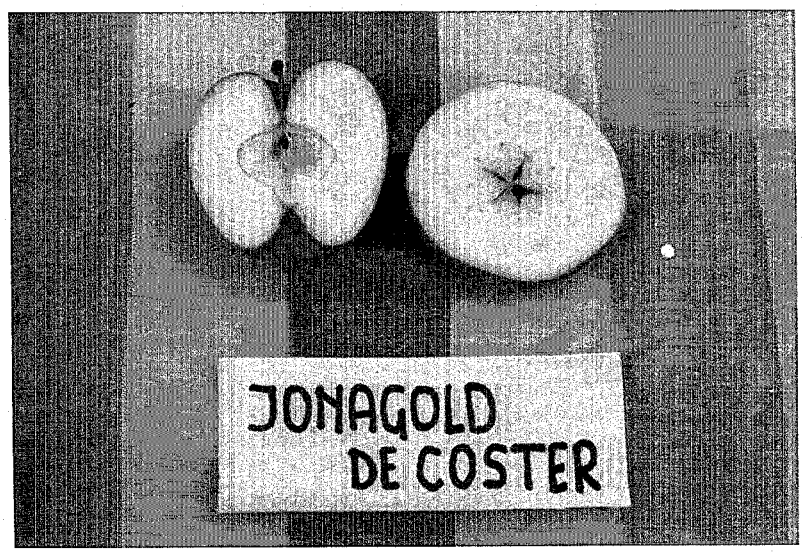
Figure 7:
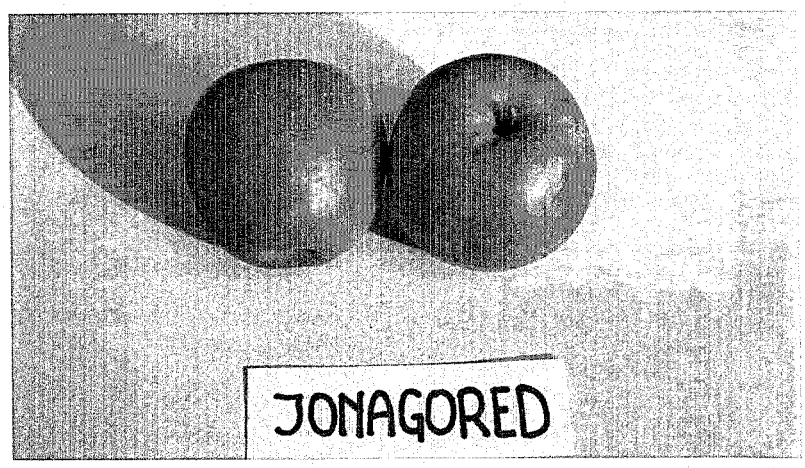
FIGS. 7, 8 and 9 are detailed views of the reference Jonagold strains, Jonagored, Rubinstar and Jonica.
Figure 8:
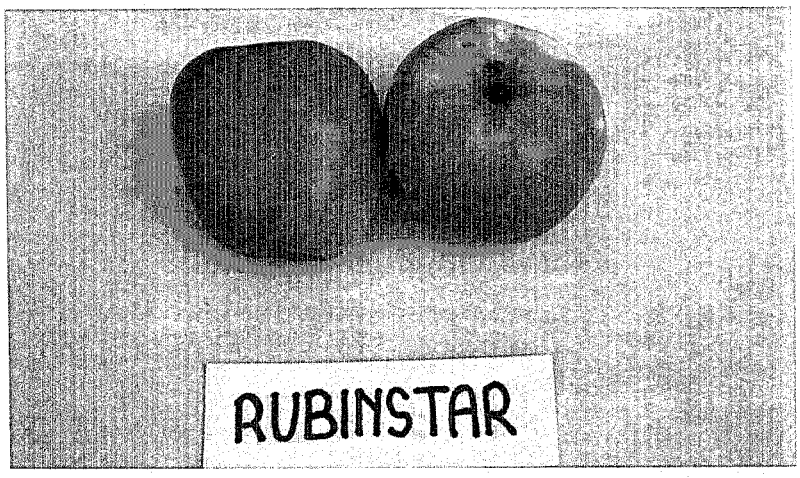
Figure 9:
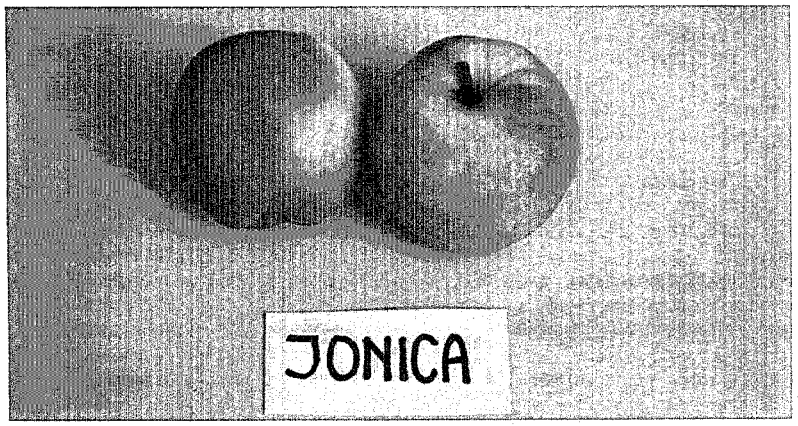
Figure 10:
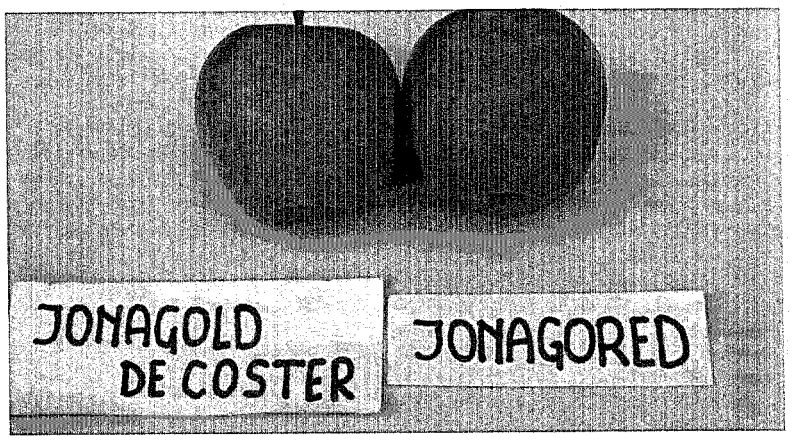
FIGS. 10, 11 and 12 are comparative displays illustrating the appearance of the new apple variety in comparison with that of the reference Jonagold mutations Jonagored, Rubinstar and Jonica.
Figure 11:
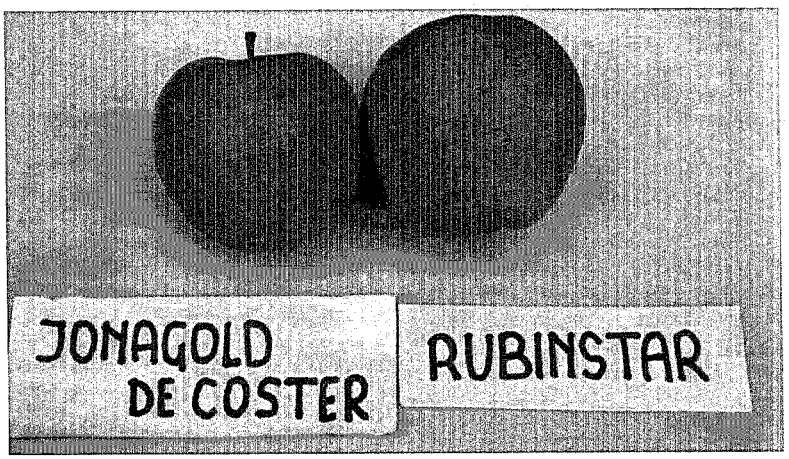
Figure 12:
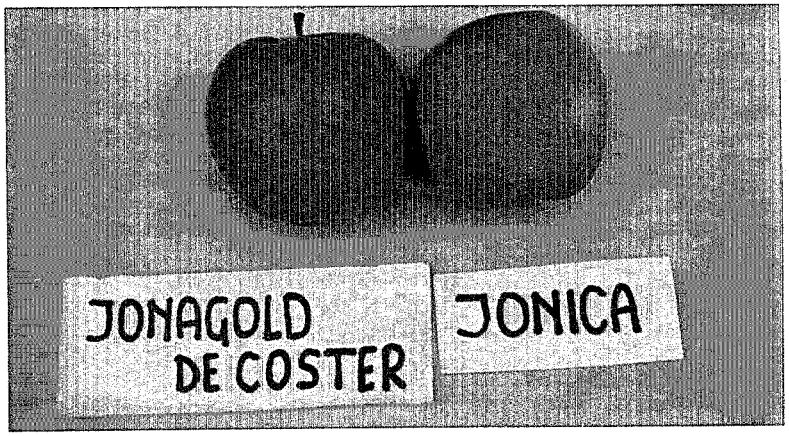

In greater detail, the characteristics of the newly discovered Jonagold De Coster apple tree variety are as follows:

Tree: Upright, rather vigorous with wide spreading branches, medium in size, not as strong as Golden Delicious.

*Bearing habit.*—Medium size, regular annular bearer, highly productive.

*Trunk.*—Thick, upright, smooth, gray color.

*Branches.*—Moderately thick, strong wide angles, very spreading, smooth gray bark.

*Leaves.*—Very large, medium to dark green with green veins.

*Spurs.*—Strong, closely set.

*Bark.*—Gray, a somewhat lighter shade than standard Jonagold. This contrasts with the bark of the Jonagored variety which is a darker shade of brown than that of standard Jonagold.

*Lenticels.*—Gray, obscure.

*Disease status.*—Virus free; susceptible to scab and mildew.

*Vigor.*—The same as standard virus-free Jonagold. This compares with the vigor of Jonagored which is 15–30% less than standard due to the expression of apple rubbery wood virus.

*Productivity.*—Same as virus free Jonagold, but greater than Jonagored.

*Pollination.*—Bloom is mid-season. The variety is triploid with sterile pollen. Can be pollinated by: Alkmene, Benoni, Cox's Orange Pippin, Delcorf, Discovery, Elan, Elise, Elstar, Fiesta, Gala, Gloster, James Grieve, Lombarts Calville, Melrose, Rafzubin, Vista Bella, Zoeta Oranje.

Fruit:

*Shape.*—Large fruit, high conical shape with the thickest point at half of the height, often leaning over going to the calyx end, very slightly ribbed.

*Stem.*—Long, 25 to 35 mm, thin.

*Cavity.*—Medium, obtuse, broad, shallow, light russet on some.

*Calyx.*—Large to medium large, closed, quite shallow.

*Lobes.*—Medium, broad, obtuse.

*Basin.*—Medium, wide obtuse, furrowed.

*Skin.*—Smooth, glossy, medium thickness and toughness.

*Color.*—Uniform bright wine red up into calyx and cavity, background color is yellow to light red, uniform pink-reddish nature begins in July covering a major portion of the fruit (80–95%) with finishing tone appearing in early September.

*Lenticels.*—Numerous, tan, obscure, almost invisible, very small points.

*Calyx tube.*—Long, narrow, funnel-shaped.

*Stamen.*—Median.

*Core.*—Small and round, closed.

*Seeds.*—Large, wide, tan to auburn.

*Flesh.*—White-yellow to yellow, firm, crisp, medium texture, juicy, sweet to aromatic-sour taste with outstanding flavor.

*Quality.*—Very good to excellent.

*Storage.*—Can be stored in regular cold storage until January and in ultra-low oxygen storage until July.

Further comparisons of the characteristics of my new apple variety Jonagold De Coster with standard Jonagold and the more significant Jonagold mutants, Jonagored, Rubinstar, Daliguy and Jonica (Schneica) are tabulated as follows:

TABLE I

| Tree | Jonagold De Coster | Jonagored |
|---|---|---|
| growth | upright<br>rather vigorous | vigorous |
| Bearing habit | regular annual bearer | regular annual bearer |
| Trunk and branches | moderately thick<br>No spur growth | moderately thick |
| bark color | grey | dark brown |
| vigor | same as standard VF | Jonagored grows 5–10% more than standard VF |
| productivity | 100% | 90% |
| **Tree** | **Standard VF Jonagold** | **Rubinstar** |
| growth | upright<br>less vigorous | less upright<br>much less vigorous |
| Bearing habit | tendency to biannual | regular annual bearer |
| Trunk and branches | moderately thick | thin |
| bark color | dark grey | very dark grey |
| vigor | | virusinfected grows 10% less than Standard VF |
| productivity | 100% | 80% |
| **Tree** | **Daliguy** | **Jonica** |

TABLE I-continued

| | | |
|---|---|---|
| growth | upright<br>less vigorous | less upright<br>much less vigorous |
| Bearing habit | tendency to biannual | regular annual bearer |
| Trunk and branches | moderately thick | tin |
| bark color | dark grey | grey |
| vigor | same as<br>Standard VF | VF grows<br>10% less than<br>Standard VF |
| productivity | 90% | 80% |

TABLE II

| | PICKING DATE | % FIRST PICK |
|---|---|---|
| Jonagold De Coster | 9.19.1990 | 65.8 |
| Jonagored | 9.19.1990 | 61.8 |
| Standard Jonagold | 9.19.1990 | 20.0 |
| Rubinstar | 9.24.1990 | 86.5 |
| Daliguy | 9.19.1990 | 30.0 |
| Jonica | 9.26.1990 | 60.9 |

TABLE III

| Fruit | Jonagold De Coster | Jonagored |
|---|---|---|
| Shape | not as large more<br>uniform in size<br>globose conical | very large<br>not uniform<br>size<br>oblongconical |
| Stem | long | long |
| Calyx | quite shallow<br>closed | shallow<br>some half-open |
| Cavity | broad<br>medium deep | rather small<br>medium to<br>little deep |
| Skin | smooth | smooth |
| Color | uniform wine-red<br>background green<br>to yellow when<br>ripe little<br>striping | dark red to<br>purple<br>little to no<br>background<br>striping |
| Lenticels | numerous | numerous |
| Calyx tube | long narrow | long narrow |
| Core | small and round | small and<br>round |
| Seeds | large wide | large wide |
| Flesh | white yellowish | yellowish |
| **Fruit** | **Standard Jonagold** | **Rubinstar** |
| Shape | large<br>not uniform in size<br>globose conical | smaller<br>more uniform in<br>size<br>flat globose |
| Stem | Long | medium long |
| Calyx | shallow<br>some half-open | quite shallow<br>some half-open |
| Cavity | broad<br>medium to deep | broad<br>medium deep |
| Skin | smooth | very smooth |
| Color | tomato red with a<br>green to yellow<br>background<br>little stripes | unform dark<br>red with very<br>little green<br>background |
| Lenticels | less | less |
| Calyx tube | not so long narrow | long narrow |
| Core | small and round | not small, and<br>flat |
| Seeds | large wide | very small and<br>very thin |
| Flesh | yellowish | yellowish |
| **Fruit** | **Daliguy** | **Jonica** |
| Shape | large<br>not uniform in size<br>globose conical | rather large<br>not uniform<br>in size<br>flat globose |
| Stem | long | medium long |
| Calyx | shallow<br>some half-open | shallow<br>closed |
| Cavity | broad | rather small |

TABLE III-continued

| | | |
|---|---|---|
| | medium to deep | medium to<br>little deep |
| Skin | smooth | very smooth |
| Color | intense tomato red<br>with a green to<br>yellow background | dull brown red<br>to pink red<br>with green<br>to yellow<br>background |
| Lenticels | less | less |
| Calyx tube | not so long, narrow | short wide |
| Core | small and round | not small and<br>flat |
| Seeds | large wide | very large,<br>very wide |
| Flesh | yellowish | white yellowish |

TABLE IV

| | Blooming period | | | | | | | | |
|---|---|---|---|---|---|---|---|---|---|
| mutation | 1989 | | | 1990 | | | 1991 | | |
| | A | B | C | A | B | C | A | B | C |
| Jonagold De-Coster | 5/02 | 5/05 | 5/14 | 4/12 | 4/16 | 5/09 | 4/17 | 4/26 | 5/13 |
| Jonagored | 4/20 | 4/29 | 5/14 | 4/11 | 4/15 | 5/08 | 4/16 | 4/23 | 5/09 |
| Jonica | 4/19 | 5/02 | 5/15 | 4/11 | 4/17 | 5/07 | 4/15 | 4/23 | 5/08 |
| Rubinstar | 4/19 | 5/02 | 5/14 | 4/11 | 4/16 | 5/08 | 4/17 | 4/23 | 5/09 |

A: bloom start
B: full bloom
C: end of bloom

TABLE V

| | Trunk growth in cm on rootstock M9 | | | | |
|---|---|---|---|---|---|
| Mutation | Planting date | 1989 | 1990 | 1991 | total |
| Jonica | 1988 | 3.22 | 1.65 | 3.41 | 8.28 |
| Jonagored | replanted 1988 | 2.18 | 1.49 | 3.63 | 7.30 |
| Rubinstar | replanted 1988 | 1.16 | 1.30 | 2.84 | 5.30 |
| Jonica | replanted | 0.97 | 1.34 | 2.84 | 5.15 |
| Jonagold De Coster | 1989 | 2.56 | 2.22 | 3.46 | 8.24 |

Trunk diameter is measured 30 cm above the ground.

TABLE VI

| | Taste | | | | |
|---|---|---|---|---|---|
| Total value for internal characteristics | 2 × aroma + 2 × sour-sweet proportion + 2 × firmness + 2 × juiciness | | | | |
| Mutant | Aroma | Sour-Sweet proportion | Firmness | Juiciness | Total Value |
| Jonica | 5,48 ± 0,44* | 5,87 ± 0,41 | 5,88 ± 0,33 | 6,36 ± 0,42 | 47,19 ± 2,57 |
| Decoster | 5,65 ± 0,41 | 6,26 ± 0,41 | 6,32 ± 0,34 | 6,25 ± 0,49 | 48,96 ± 2,62 |
| Rubinstar | 5,39 ± 0,41 | 6,0 ± 0,40 | 6,09 ± 0,38 | 6,43 ± 0,42 | 47,83 ± 2,38 |
| Jonagored | 5,30 ± 0,40 | 5,43 ± 0,45 | 5,68 ± 0,38 | 5,67 ± 0,44 | 44,17 ± 2,56 |

TABLE VII

| | Surface Color | |
|---|---|---|
| Group | Mutant | Identification Mark |
| Group 1 | Jonica | Bright-red blush with green ground color |
| Group 2 | De Coster | Group in between from bright-red to dark-red with green ground color |
| Group 3 | Jonagored | Dark-red; little to no |

TABLE VII-continued

| Group | Mutant | Surface Color Identification Mark |
|---|---|---|
| | | green ground color |

TABLE VIII

COMPARISON OF JONAGOLDMUTANTS
(Selective sample of 5 apples)

Appearance: * Color:

| | |
|---|---|
| Jonica: | uniform colored, dull brown red, the color changes gradually from green to red, the green side is green over the whole length. |
| Jonagored: | dark red to purple, striped, almost no green color, change from green to red is very diffuse. |
| Rubinstar: | uniform dark red, little green ground color, change from green to red is diffuse. |
| DeCoster: | between bright and dark red, lightly striped, change from red to green is diffuse and not over the whole length. |
| Lenticels: | DeCoster & Jonagored have many lenticels; Rubinstar and Jonica have a moderate number of lenticels. |
| Shape: | Jonica and Rubinstar are rounded quadrangular; Jonagored: asymetrical; DeCoster: a little higher, a little sloping. |

| | | |
|---|---|---|
| Average number of pips: | Jonica: | 3,0 |
| | Jonagored: | 2,6 |
| | Rubinstar: | 4,0 |
| | DeCoster: | 2,6 |
| Diameter of core: | Jonica: | 2,76 cm |
| | Jonagored: | 2,88 cm |
| | Rubinstar: | 3,18 cm |
| | DeCoster: | 3,0 cm |

Jonagored

| Height | Width | Height/Width |
|---|---|---|
| 72,84 | 82,02 | 0,89 |
| 66,09 | 75,31 | 0,88 |
| 69,70 | 77,22 | 0,50 |
| 76,77 | 84,12 | 0,91 |
| 74,01 | 78,95 | 0,94 |
| | | 0,90 = Average |

- Dark red to purple-red colored
- striped coloring
- little to no green ground color
- nose mostly red colored
- many lenticels.

Rubinstar

| Height | Width | Height/Width |
|---|---|---|
| 78,24 | 80,86 | 0,97 |
| 69,72 | 75,92 | 0,92 |
| 74,64 | 81,60 | 0,91 |
| 78,13 | 78,76 | 0,99 |
| 75,98 | 78,93 | 0,96 |
| | | 0,95 = Average |

- Dark red (in 1991 less dark than in 1989 and 1990)
- homogeneously colored
- little to no green ground color
- moderate number of lenticels.

DeCoster

| Height | Width | Height/Width |
|---|---|---|
| 67,07 | 71,52 | 0,94 |
| 73,50 | 75,60 | 0,97 |
| 69,38 | 78,78 | 0,88 |
| 68,86 | 75,16 | 0,92 |
| 67,15 | 79,25 | 0,85 |
| | | 0,91 = Average |

- Between bright red and dark red
- striped coloring
- much surface is green colored
- at one side less high
- many lenticels.

Jonica

| Height | Width | Height/Width |
|---|---|---|
| 68,48 | 73,05 | 0,94 |
| 72,46 | 75,69 | 0,96 |
| 70,94 | 74,77 | 0,95 |
| 68,82 | 74,56 | 0,92 |
| 72,32 | 79,26 | 0,91 |
| | | 0,94 = Average |

- Bright red
- homogeneously colored
- moderate number of lenticels
- nose may be green
- much surface is green colored.

(Source: Gegevens van de Nationale Proeftuin voor Grootfruit, Sint-Truiden)

In summary, the unique characteristics of my newly discovered apple tree variety Jonagold De Coster are as follows:

The unique and striking color of the fruit, between dark and bright red.

Its original and continued virus free-status.

A high percentage of early first pick.

A vigorous and highly productive tree growth habit, creating a large tree volume with a very large potential fruit-bearing surface, which is well used.

Good fruit storage properties.

Superior fruit flavor.

I claim:

1. The new and distinct variety of apple tree as described and illustrated characterized particularly by the unique color of its fruit, by its unique virus free condition from inception, and characterized further by its high percentage of early first pick, a vigorous and highly productive tree growth habit, good fruit storage properties, and superior fruit flavor.

* * * * *